US012758351B2

(12) United States Patent
Allen

(10) Patent No.: US 12,758,351 B2
(45) Date of Patent: Oct. 13, 2026

(54) OPERATING ROOM EQUIPMENT FOR OPHTHALMIC SURGERY

(71) Applicant: Alcon Inc., Fribourg (CH)

(72) Inventor: Douglas Allen, Santa Barbara, CA (US)

(73) Assignee: Alcon Inc., Fribourg (CH)

( * ) Notice: Subject to any disclaimer, the term of this patent is extended or adjusted under 35 U.S.C. 154(b) by 407 days.

(21) Appl. No.: 18/449,275

(22) Filed: Aug. 14, 2023

(65) Prior Publication Data

US 2024/0058089 A1 Feb. 22, 2024

Related U.S. Application Data

(60) Provisional application No. 63/399,134, filed on Aug. 18, 2022.

(51) Int. Cl.

| | |
|---|---|
| ***A61B 90/25*** | (2016.01) |
| ***A61B 34/00*** | (2016.01) |
| ***A61B 50/26*** | (2016.01) |
| ***A61F 9/007*** | (2006.01) |
| ***A61G 13/10*** | (2006.01) |
| *A61B 17/00* | (2006.01) |
| *A61B 90/00* | (2016.01) |

(52) U.S. Cl.

CPC .............. *A61B 90/25* (2016.02); *A61B 34/25* (2016.02); *A61B 50/26* (2016.02); *A61F 9/00745* (2013.01); *A61G 13/107* (2013.01); *A61B 2017/00973* (2013.01); *A61B 2090/0805* (2016.02); *A61B 2090/373* (2016.02); *A61B 2217/005* (2013.01)

(58) Field of Classification Search

CPC ......... A61B 90/25; A61B 34/25; A61B 50/26; A61B 2017/00973; A61B 2090/0805; A61B 2090/373; A61B 2217/005; A61B 2090/3735; A61F 9/00745; A61G 13/107; A61G 12/007; A61G 15/02

See application file for complete search history.

(56) References Cited

U.S. PATENT DOCUMENTS 5,122,904 A * 6/1992 Fujiwara ................ A61B 90/25 206/316.1
5,332,181 A 7/1994 Schweizer
6,661,571 B1 * 12/2003 Shioda .................. A61B 50/13 359/368

(Continued)

*Primary Examiner* — Ashley L Fishback
*Assistant Examiner* — Chima U Igboko

(57) ABSTRACT

Particular embodiments disclosed herein provide operating equipment including a base for resting on a floor. A boom extends upwardly from a central base and extends outwardly from the central base in a forward direction. A gantry is suspended from the boom and has three or more degrees of freedom. A surgical instrument, such as a surgical microscope, is mounted to the gantry. One or more electrical components are mounted in the central base and are configured to support performing ophthalmic surgery, such as a computing device and vacuum pump. A surgical chair mounts to an arcuate track in a base and is slidable along the track. The surgical chair has adjustable arms secured thereto for holding surgical equipment. A patient bed incorporates a storage device and a coupler that engages a corresponding coupler coupled to a computing device in the base for downloading patient data from the storage device.

15 Claims, 8 Drawing Sheets

(56) References Cited

U.S. PATENT DOCUMENTS

| | | | | |
|---|---|---|---|---|
| 2008/0269602 | A1* | 10/2008 | Csavoy | A61B 34/20 600/426 |
| 2008/0303351 | A1* | 12/2008 | Jansen | H02J 50/12 307/104 |
| 2013/0267964 | A1 | 10/2013 | Rogers | |
| 2017/0000575 | A1* | 1/2017 | Griffiths | A61B 50/10 |
| 2017/0304020 | A1* | 10/2017 | Ng | A61B 34/20 |
| 2019/0167377 | A1* | 6/2019 | Hirose | G02B 21/0012 |
| 2021/0297560 | A1 | 9/2021 | Luna | |
| 2022/0211464 | A1 | 7/2022 | Matsuda | |

* cited by examiner

OPERATING ROOM EQUIPMENT FOR OPHTHALMIC SURGERY

TECHNICAL FIELD

The present disclosure relates generally to equipment for facilitating performance of ophthalmic surgery.

BACKGROUND

Many disorders of the eye are treatable with ophthalmic surgery. Defects of the crystalline lens, such as cataracts, may be corrected by replacement of the crystalline lens with an artificial intraocular lens (IOL). Disorders of the retina may also be corrected through various surgical procedures. The eye is extremely delicate and the anatomy operated upon are extremely small. Therefore, ophthalmic surgery is performed in a highly-controlled environment with sophisticated equipment.

BRIEF SUMMARY

The present disclosure relates generally to operating room equipment for supporting ophthalmic surgery.

Particular embodiments disclosed herein include operating equipment including a base for resting on a floor. A boom extends upwardly from the base and extends outwardly from the base in a forward direction. A gantry is suspended from the boom and has three or more degrees of freedom. A surgical instrument is mounted to the gantry. One or more electrical components are mounted in the base and are configured to support performing ophthalmic surgery.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

In prior approaches to performing ophthalmic surgery, many pieces of equipment are needed, each with its own power cord, housing, and possibly other features, such as vacuum tubes. As a result, the operating room can become cluttered and present many tripping hazards.

In the operating equipment disclosed herein a boom is mounted to a base housing one or more computing device, vacuum pumps, and possibly other equipment. A gantry is mounted to the boom and surgical equipment may be mounted to the gantry, such as a surgical microscope and one or more displays. A surgical chair is mounted to an arcuate path such that the chair may readily be moved to the left or right of a patient bed or superior to the patient bed. The chair has adjustable arms mounted thereto for holding additional pieces of equipment, such as a holder for a phaco-vit handpiece, a scanner for surgical instruments, and/or an additional display. The patient bed may have a storage device and electrically connect to a computing device in the base in order to transfer and receive patient data for an ophthalmic surgery.

Figure 1A:
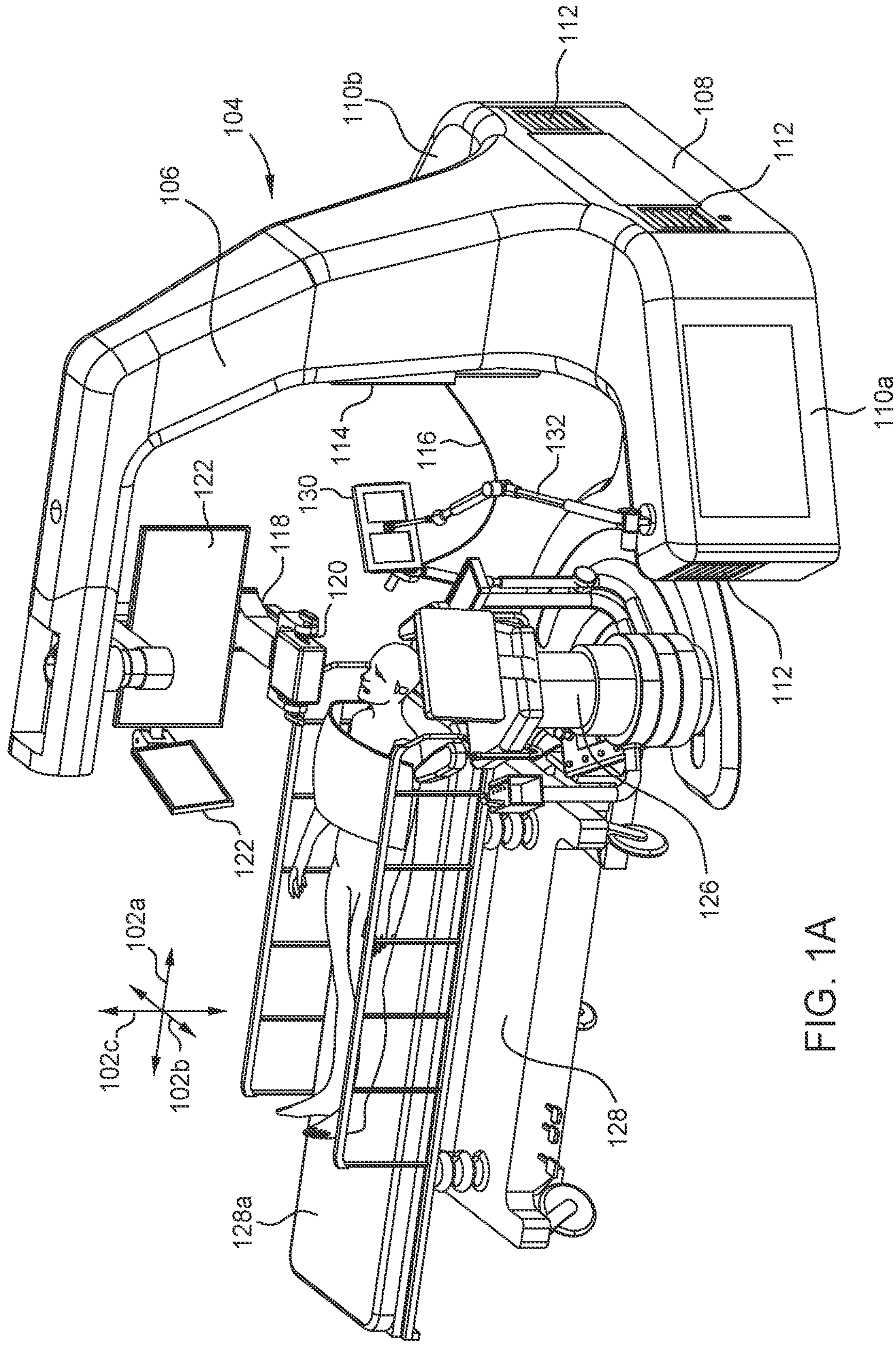
FIG. 1A is an isometric view of operating room equipment for supporting ophthalmic surgery, in accordance with certain embodiments.
Figure 1B:
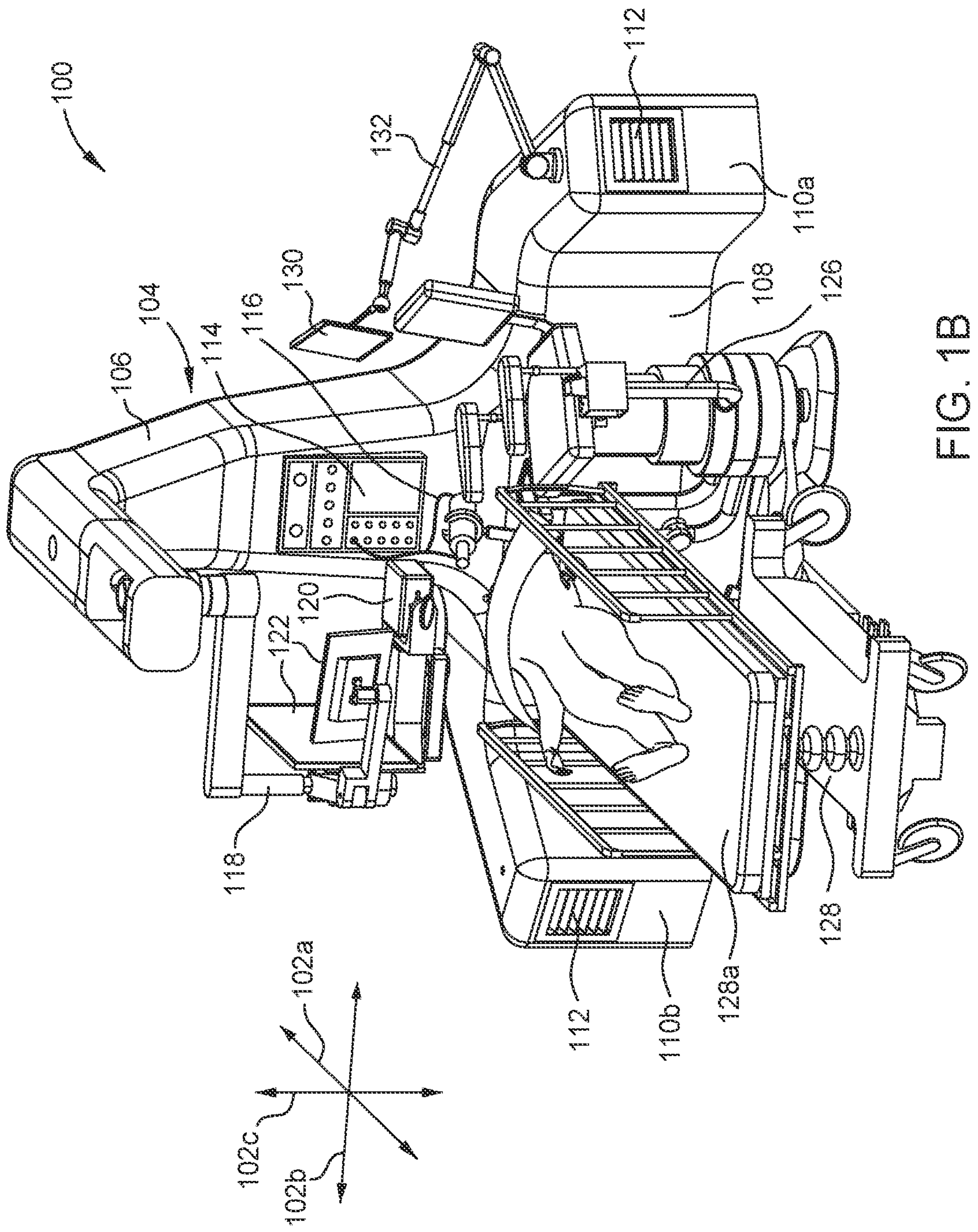
FIG. 1B is an alternative isometric view of the operating room equipment of FIG. 1A.

FIG. 1 illustrates operating room equipment 100 that may be used to support the performance of ophthalmic surgery. The operating room equipment 100 may be understood with respect to a longitudinal direction 102*a*, a transverse direction 102*b*, and a vertical direction 102*c* that are all mutually perpendicular to one another. The vertical direction 102*c* may be defined as substantially (e.g., within 2 degrees of) perpendicular to the floor of the room in which the operating room equipment 100 is located.

The operating room equipment 100 may include a support frame 104 including a boom 106. The boom 106 extends upwardly in the vertical direction 102*c* from the floor as well as extending outwardly along the longitudinal direction 102*a*, i.e. "the forward direction" as used herein. The boom 106 extends upwardly from a central base 108. The central base 108 may have sufficient weight to prevent tipping of the boom 106 including when various items of surgical equipment are suspended therefrom. The central base 108 may therefore include both a structural frame for securing to the boom 106 as well as some form of ballast, such as steel plates, concrete blocks, or other dense material.

In the illustrated embodiment, lateral bases 110*a*, 110*b* secure to the central base 108 and extend outwardly in the transverse direction 102*b* and in the forward direction to provide additional stability. The boom 106, central base 108, and lateral bases 110*a*, 110*b* may be formed of an internal frame, such as a steel frame, covered in a shell, such as a shell made of one or more plastic panels.

The lateral bases 110*a*, 110*b* may cooperate with the weight of the central base 108 to resist tipping of the boom 106. However, in some implementations, the lateral bases 110*a*, 110*b* are either omitted or detachable such that the central base 108 alone is sufficient to prevent tipping. In still other embodiments, the central base 108 or boom 106 may be anchored to the floor, wall, column, or other structure to prevent tipping.

Figure 6:
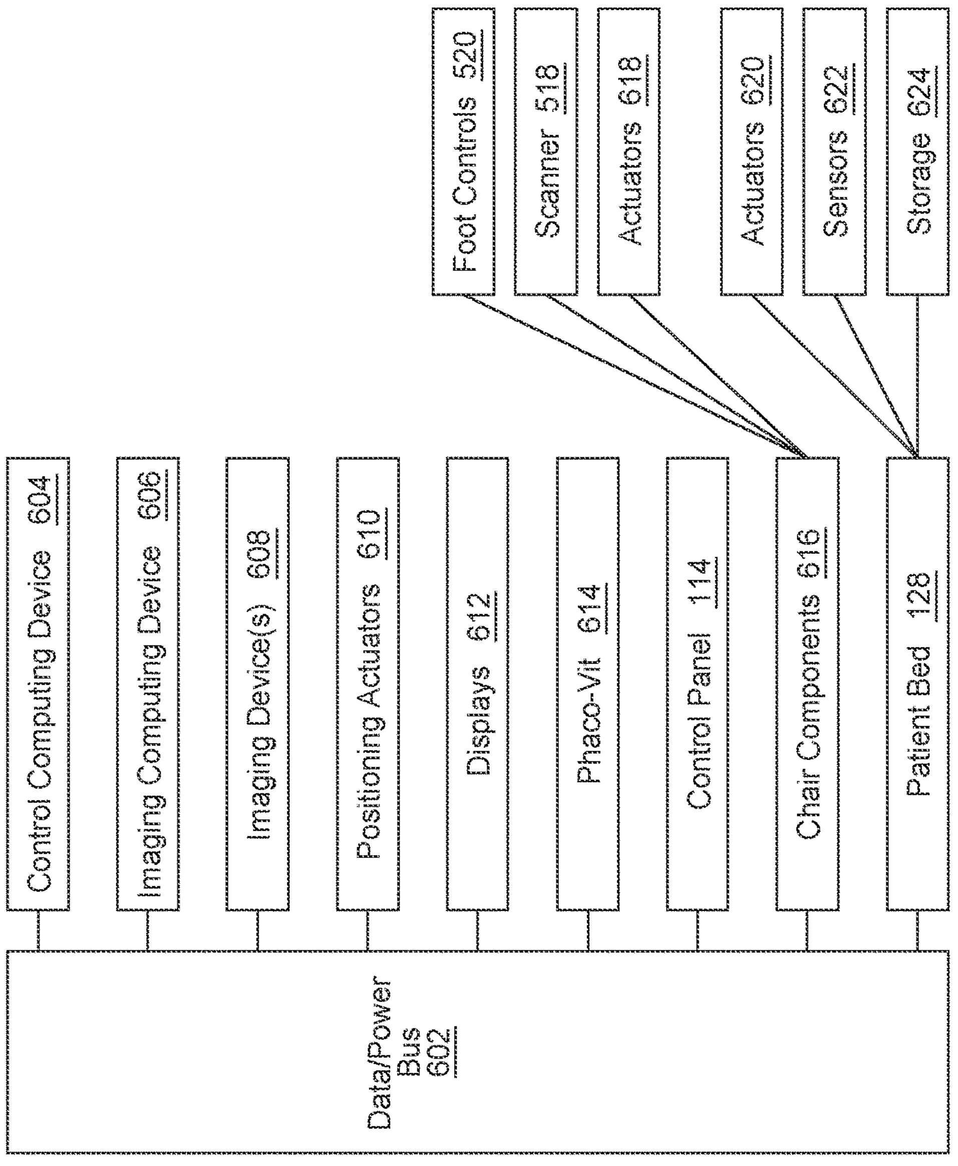
FIG. 6 is a schematic block diagram of components of the operating room equipment, in accordance with certain embodiments.

The central base 108 and lateral bases 110*a*, 110*b* may be hollow and provide a cavity for housing computing devices, power adapters, power distribution wires, vacuum pumps, and other components (see FIG. 6 and associated description). The weight of such components may add to the stability and resistance to tipping provided by the central base and lateral bases 110*a*, 110*b*. The central base 108 and lateral bases 110*a*, 110*b* may have vents 112 on one or more surfaces thereof to facilitate rejection of heat generated by such components. One or more fans may also be housed within some or all of the central base 108 and lateral bases 110*a*, 110*b* to promote air flow through the vents 112. In some implementations, the air flow induced by the one or more fans exhausts out of the rearward side of the central base 108 and/or lateral bases 110*a*, 110*b* in order to avoid blowing dust onto, or otherwise disturbing, performance of an ophthalmic surgery on the forward side of the central base 108. The rearward side may face in a rearward direction opposite the forward direction. A power cord for powering components mounted within the central base 108 may also extend from the rearward side of the central base 108 thereby avoiding a tripping hazard on the forward side of the central base 108.

The boom 106 may have a control panel 114 mounted thereto and facing in the forward direction. The control panel 114 may have controls (buttons, switches, touch screens, etc.) for controlling a vacuum tool, such as a phaco-vit tool for performing phaco-emulsification and vitrectomy. The control panel 114 may further define connectors for connecting to hoses 116 of the vacuum tool. The control panel 114 may further define physical connectors or a wireless interface for receiving inputs from another device, such as a foot pedal. The control panel 114 may be connected to a vacuum pump housed within the central base 108 and control the vacuum pump according to control inputs received by the control panel 114.

A gantry 118 secures to the boom 106 and extends downwardly from the boom 106 in the vertical direction 102*c*. The gantry 118 may define one or more degrees of translation along some or all of the longitudinal direction 102*a*, transverse direction 102*b*, and vertical direction 102*c*. The gantry 118 may define one or more degrees of rotational movement, such as rotation about axes parallel to some or all of the longitudinal direction 102*a*, transverse direction 102*b*, and vertical direction 102*c*. For example, the gantry 118 may define, three or more degrees of freedom and may have up to six degrees of freedom including up to three translational degrees of freedom and up to three rotational degrees of freedom.

The gantry 118 may have various items of equipment mounted thereto, such as a surgical microscope 120 and one or more displays 122. The surgical microscope 120 and one or more displays may have computing components housed within themselves or connect to computing components housed within the central base 108. The equipment mounted to the gantry 118 may be readily removed and replaced in a modular manner. Power and data wires and tubing for connecting to equipment mounted to the gantry 118 may be routed up and through the boom 106 in order to reach components mounted within the central base 108.

The operating room equipment 100 may further include an articulated surgical chair 126 and a patient bed 128, both of which are described in greater detail below. Any number of additional displays 130 may also mount to the support frame 104, such as to one or both of the lateral bases 110*a*, 110*b* by means of a gantry 132 having one or more articulated joints each with from one to six degrees of freedom. The displays 130 may be connected by wires or wireless connections to computing components housed within the central base 108.

Figure 2A:
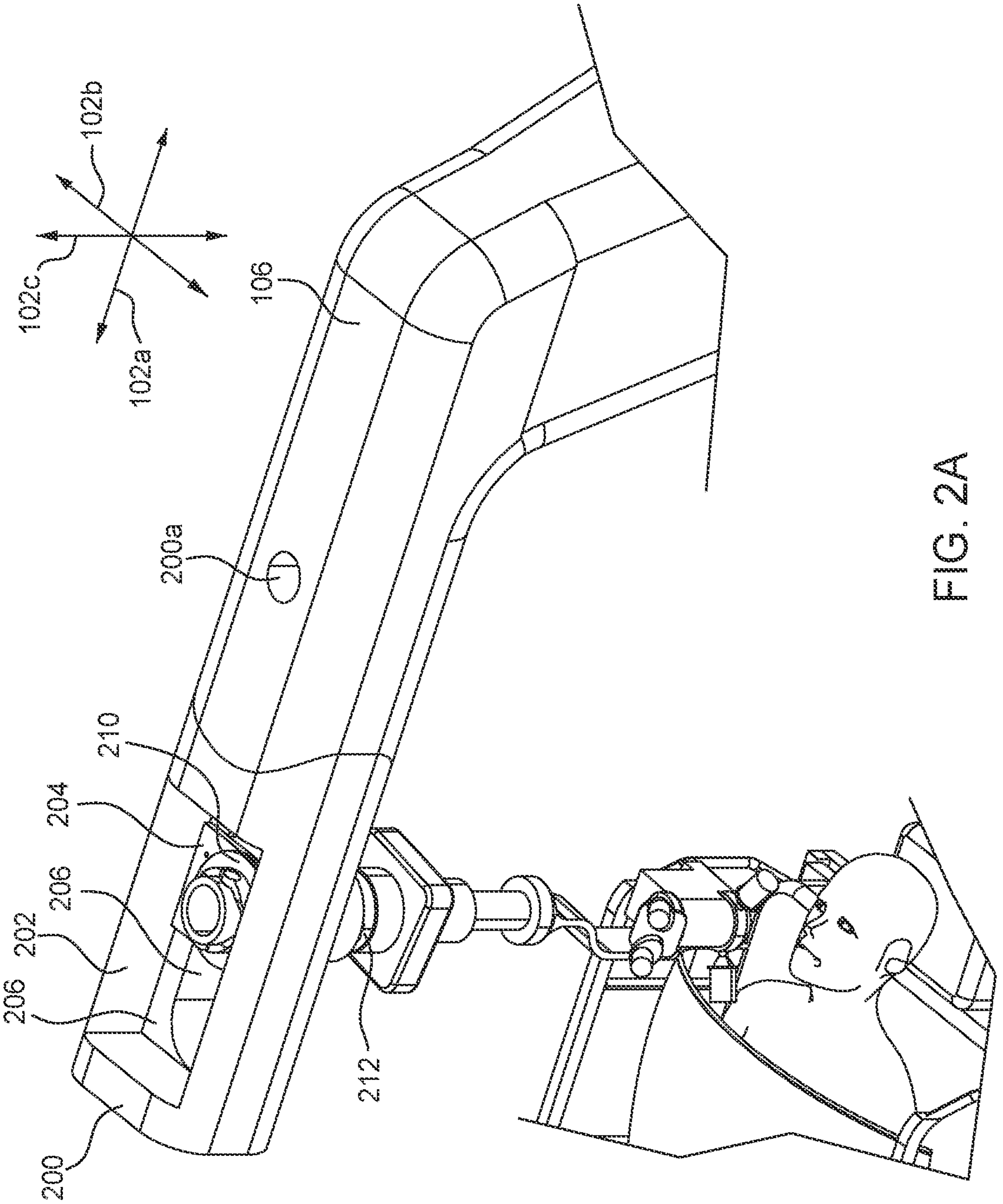
FIG. 2A is an isometric view of an articulated boom arm for supporting a surgical microscope, in accordance with certain embodiments.
Figure 2C:
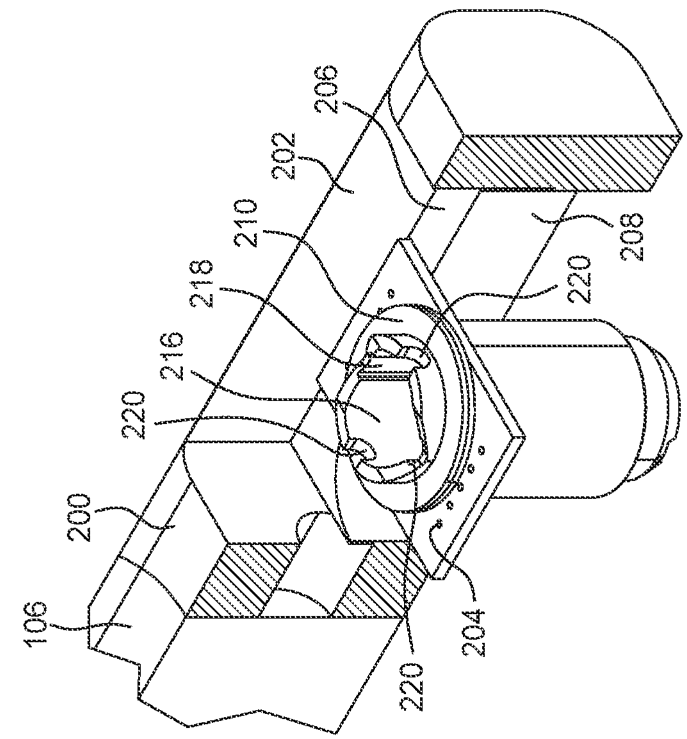
FIGS. 2B and 2C are cutaway views of the articulated boom arm of FIG. 2.
Figure 2B:
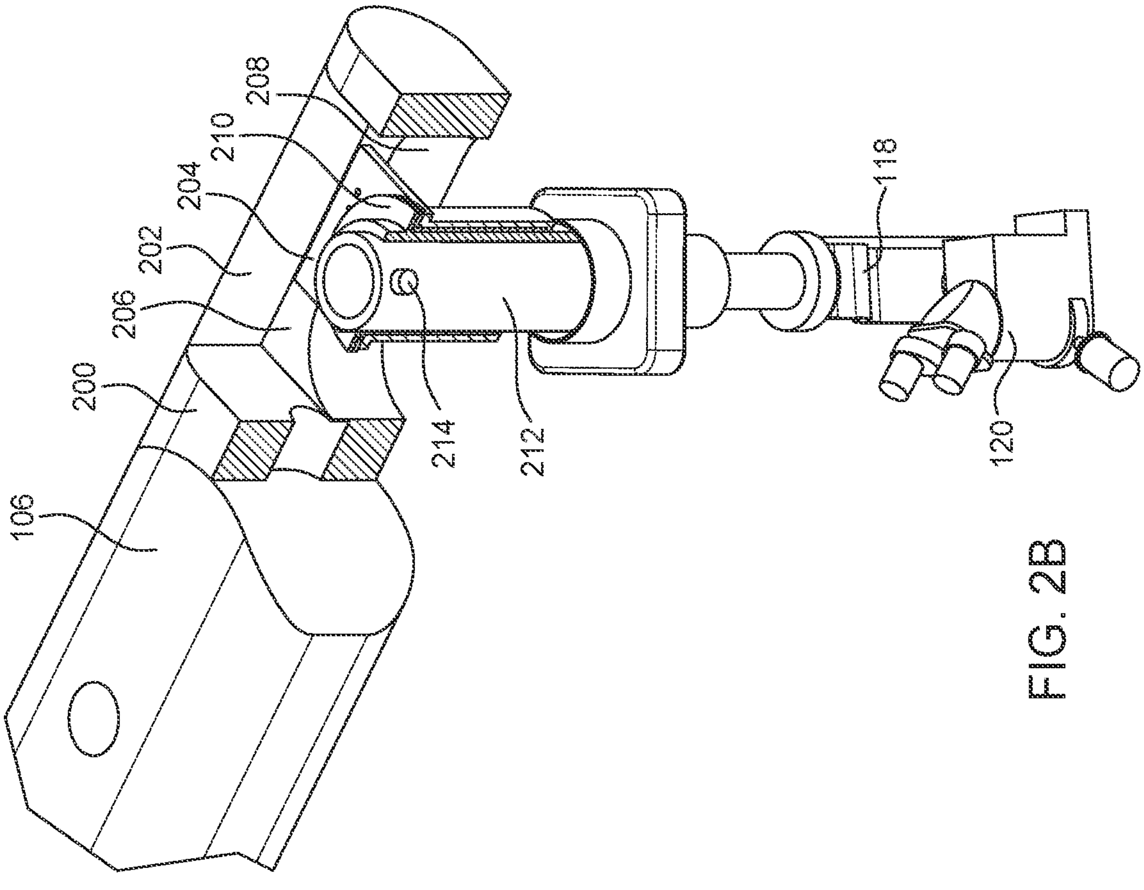

FIGS. 2A, 2B, and 2C illustrate structures for mounting the gantry 118 to the boom 106. The one or more displays 122 may mount to the boom 106 in a like manner. In the illustrated embodiment, a rotatable member 200 is mounted to a distal end of the boom 106 and is rotatable relative to the boom 106. For example, the rotatable member 200 may be rotatable about an axis substantially (e.g., within 5 degrees of) parallel to the vertical direction 102*c*, such as about pivot point 200*a*. As is apparent, the point of attachment of the gantry 118 may be offset from the pivot point 200*a*. In some embodiments, the rotatable member 200 is omitted and a distal portion of the boom 106 has the gantry 118 mounted thereto using the structures described below with respect to the rotatable member 200.

The rotatable member 200 may define a slot 202, such as a slot 202 having a long dimension thereof substantially (e.g., within 5 degrees of) parallel to the longitudinal direction 102*a*. A plate 204 or other structure may be slidably mounted on or in the slot 202 and be slidable along the slot 202 in the longitudinal direction 102*a*. In the illustrated embodiment, a floor 206 extends inwardly from the slot 202 in the transverse direction 102*b* and defines an inner slot 208. The plate 204 may therefore rest on the floor 206 and be slidable along the floor 206.

A collar 210 may be rotatably mounted to the plate 204 and extend into the inner slot 208 and be slidable within the inner slot 208. The collar 210 rotatably, and possibly removably receives, a shaft 212 to which the gantry 218 is mounted. The gantry 218 may be mounted such that an optical axis of the surgical microscope 120 (or other optical instrument) is substantially collinear (e.g., within 10 cm) and parallel (e.g., within 5 degrees) to the axis of rotation of the shaft 212. For example, the shaft 212 may have one or more pins 214 protruding outwardly therefrom and the interior 216 of the collar 210 may define one or slots 218 arranged parallel to the axis of symmetry of the interior 216 (e.g., axis of a cylinder defined by the interior 216, in a helix, or other configuration. The shaft 212 may be inserted through the collar 210 with the one or more pins 214 positioned within the one or more slots 218. The shaft 212 may then be rotated relative to the collar 210 and the pins 214 may be seated within one or more indentations 220 defined by the upper edge of the collar 210. The weight of the shaft 212, gantry 218, and any equipment mounted to the gantry 118 may then resist removal of the pins 214 from the indentations 220.

The collar 210 may be rotatable with respect to the plate 204 thereby defining a rotational degree of freedom for the gantry 118 perpendicular to the rotational degree of freedom provided by the rotatable member 200. The gantry 118 itself may then provide up to six degrees of freedom as well in order to provide fine tuning of the orientation and position of equipment secured to the gantry 218.

The boom 106, rotatable member 200, and shaft 212 are preferably sufficiently rigid to resist vibrations induced by actuators of the gantry 118 and equipment mounted thereto, such as the surgical microscope 112. In this manner, vibrations induced by adjustment of the position and/or orientation of the gantry 118 or zooming in or out with the surgical microscope 112 will be more quickly attenuated.

The combination of the pivoting of the rotatable member 200, the sliding motion of the collar 210, and rotational of the shaft 212, along with the optical axis of the surgical microscope 120 or other optical instrument being aligned with the axis of rotation of the shaft 212 may result in a relatively small lateral motions in the longitudinal and transverse directions 102*a*, 102*b* and rotational motion coaxial to the axis of rotation of the shaft 212. This facilitates ergonomically and rapidly achieving the three main surgical positions (left temporal, superior, and right temporal). Current operating room equipment requires a large range of motion to achieve the main surgical positions and often requires the equipment to move to the opposite side of the patient's bed in a slow and cumbersome process. Some operating rooms will have the patient rolled in feet first instead of head first so that equipment doesn't have to change to a different side of the bed, which is difficult so many cords and tubes on the floor.

Figure 3:
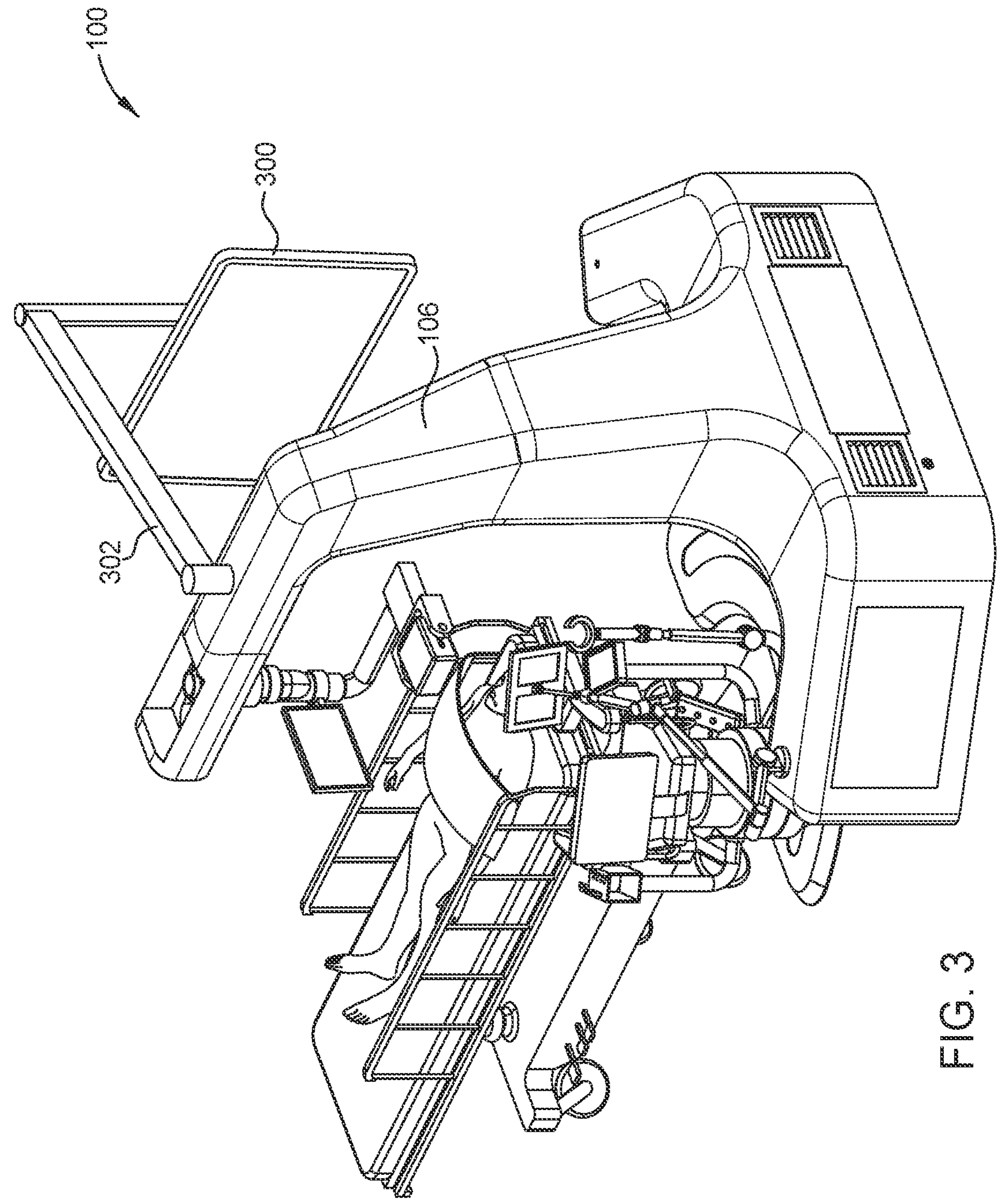
FIG. 3 is an isometric view of operating room equipment including an articulated monitor support arm, in accordance with certain embodiments.

Referring to FIG. 3, in some implementations, the operating room equipment 100 includes a large display 300, e.g., 1 meter or larger along at least one edge, that is not readily mounted to the gantry 118 due to excess weight or lack of space. The display 300 may be suspended from an arm 302 that is rotatably mounted to the boom 106, such as to a top of the boom 106.

Referring to FIGS. 4A, 4B, 4C, and 4D, the patient bed 128 may have a storage device mounted therein. The storage device may be no more than a storage device, e.g., a flash storage device, or may be a computing device incorporating the storage device. The storage device may then be loaded with patient data, such as a treatment plan to be implemented by ophthalmic surgery performed using the operating room equipment 100. The patient bed 128 may then be connected to the operating room equipment 100 and the patient data may be downloaded and used to provide guidance for the ophthalmic surgery.

Figure 4B:
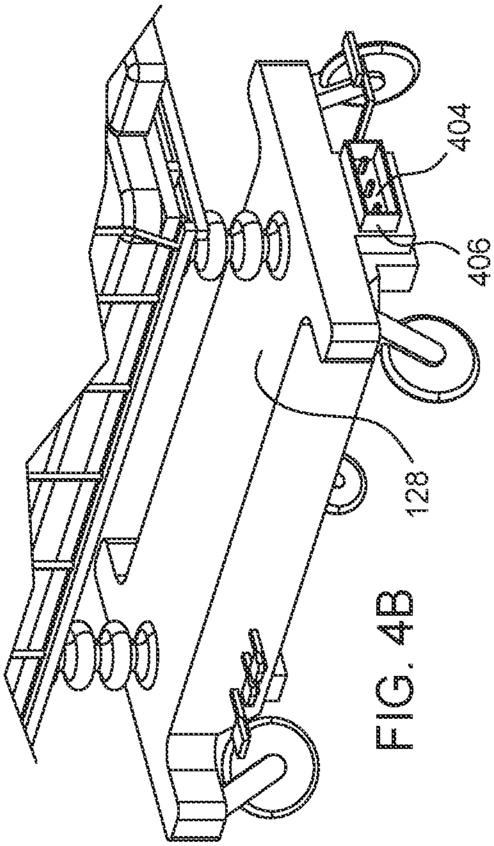
FIGS. 4A to 4D are isometric views showing electrical connectors for connecting an electronic patient bed to the operating room equipment, in accordance with certain embodiments.
Figure 4D:
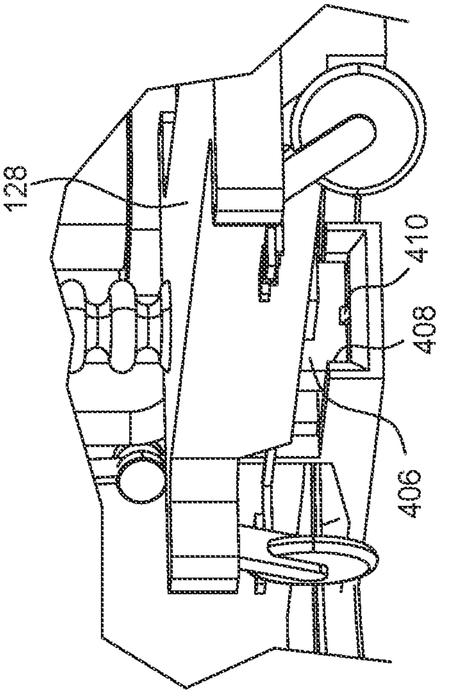
Figure 4A:
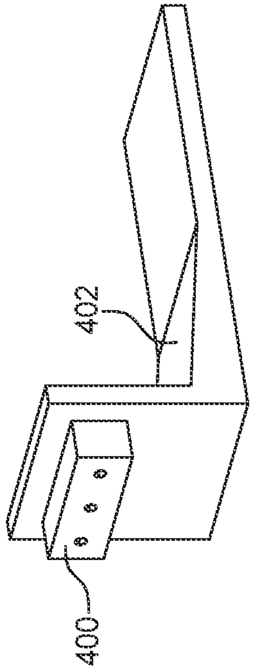

Referring specifically to FIGS. 4A and 4B, a first coupler 400, e.g., a plug, protrudes from a housing 402. The housing 402 may be secured to the base of the articulated surgical chair 126 (see discussion of FIG. 5, below), the central base 108, the floor of the operating room, or some other structure. A second coupler 404, e.g., socket, is secured to the patient bed 126, such as to a housing 406. The second coupler 404 is sized and configured to engage the first coupler 402 in order to establish a connection for supplying power to the storage device in the patient bed 126 and a data communication channel. The placement of the first coupler 400 and second coupler 404 may be reversed in some implementations. The first coupler 400 and second coupler 404 may have a proprietary arrangement of electrical connections or may use a standard configuration, such as universal serial bus (USB) or other connection standard.

Figure 4C:
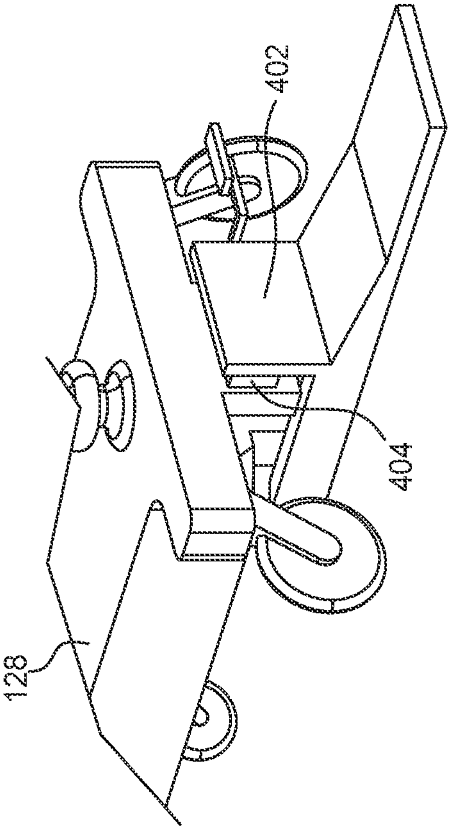

Referring to FIGS. 4C and 4D, the housing 402 may include or be secured adjacent a slot 408 for receiving the housing 406. A latch 410 may be positioned within the slot 408 and engage the housing 404. The slot 408 may be oriented to deflect the latch 410 upon insertion of the housing 404 within the slot 408 until the second coupler 404 is engaged with the first coupler 402. The latch 410 may then be biased upward and resist removal of the housing 404 from the slot 408 until the latch 410 is disengaged, i.e., deflected out of the way of the housing 404. The latch 410 may be manually actuated or connected to an electrical actuator, e.g., solenoid, that is activated by means of a button on the patient bed 126, the control panel 114, or elsewhere on the operating room equipment 100.

Figure 5:
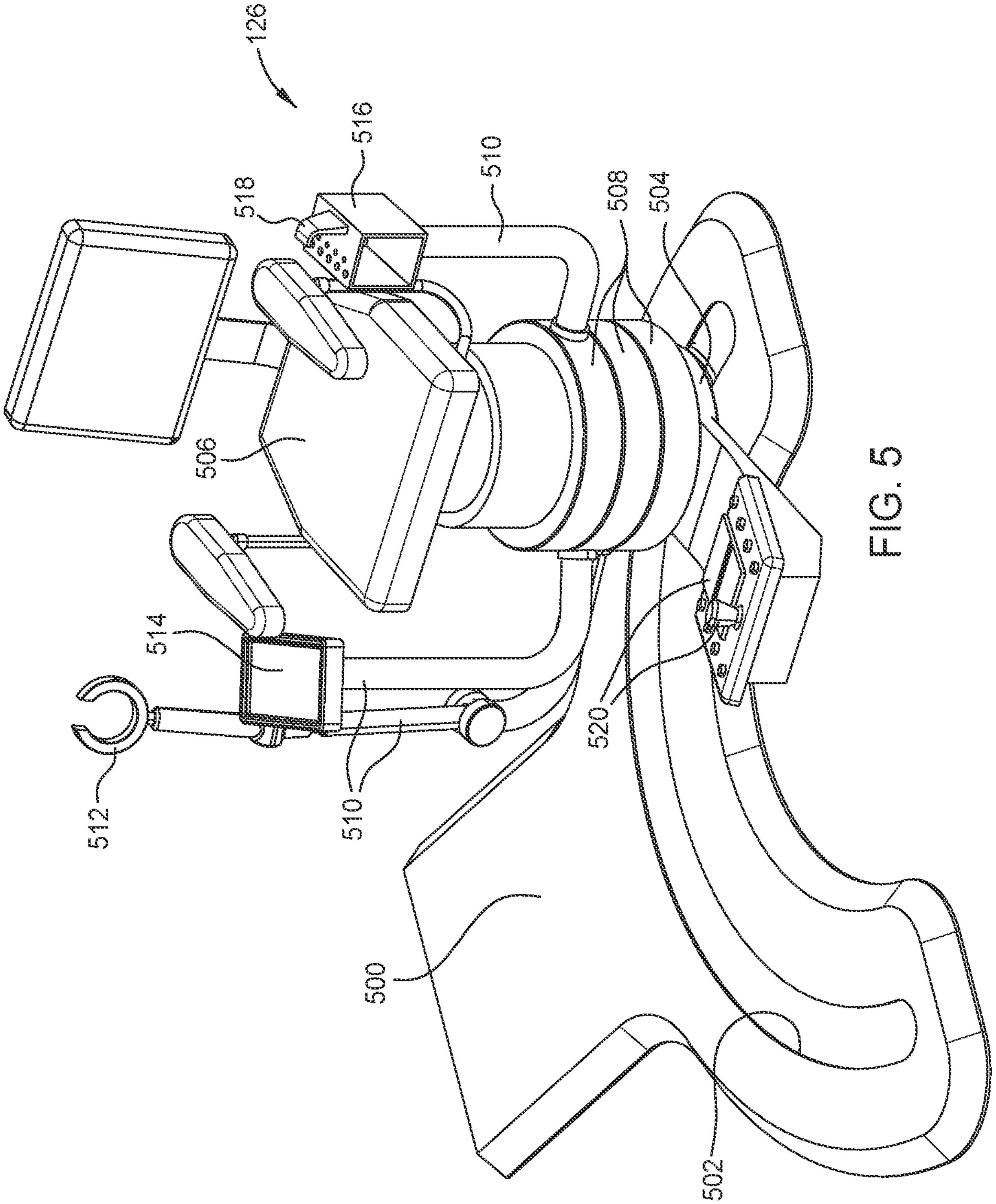
FIG. 5 is an isometric view of an articulated surgical chair, in accordance with certain embodiments.

Referring to FIG. 5, the articulated surgical chair 126 may include a base 500 having a track 502 formed thereon. The track 502 may be implemented as the illustrated arcuate slot, an arcuate rail, or other form of guide. A sliding base 504 engages the track 502 and is slidable around the track 502. A seat 506 in which a surgeon sits is mounted to the sliding base 504, such as on top of the sliding base 504. The track 502 may be shaped such that the seat 504 may be placed in various positions relative to the patient bed 128, such as left temporal, superior, and right temporal positions.

A locking mechanism may be activated by a user to lock the sliding base 504 relative to the track 502. An actuator in the base 500 or the sliding base 504 may move the sliding base 504 relative to the track 502 responsive to control inputs from a user. Alternatively, the sliding base 504 may be manually moved around the track 502. In some implementations, one or both of the gantry 118 and arm 302 may be coupled to actuators that are coordinated with the position of the sliding base 504. For example, upon sliding of the sliding base 504 to the right side of the track 502, actuators of the gantry 118 and/or coupled to the arm 302 may also rotate such that the surgical microscope 120, display 122, and/or display 300 are on the left side of the track 502, e.g., having the patient bed 126 between the sliding base 504 and the surgical microscope 120, display 122, and/or display 300.

The sliding base 504 may have structures secured thereto for mounting and positioning accessories. In the illustrated embodiment, these structures include rings 508 encircling the sliding base 504 and that are rotatable relative to the sliding base 504 and may be locked at various points along the range of rotation of the rings 508 about the sliding base 504. Each ring 508 may have one or more arms 510 extending outwardly and upwardly therefrom such that a distal end of each arm 510 is conveniently positioned to a surgeon seated within the seat 506. Each arm 510 may be adjusted to and locked into various positions with respect to one or more degrees of freedom such as extending the length of each arm 510, tilting each arm 510, and/or articulating one or more joints in each arm 510. A distal end of each arm 510 may have an accessory mounted thereto, such as a ring 512 for holding a handpiece of a phaco-vit vacuum pump, a display 514 (e.g., tablet computer), an instrument holder 516, an instrument tray, tube manager, mechanical arm, robotic arm, or other accessories. The instrument holder 516 may include a scanner 518 for scanning instruments removed from and returned to the instrument holder 516.

The sliding base 504 may have one or more foot controls 520 mounted thereto and positioned to be contacted by the surgeon when seated within the seat 506. The foot controls 520 may be fixed to the sliding base 504 and translate therewith. The foot controls 520 may include foot controls for controlling any of the components forming part of the operating room equipment 100. For example, the foot controls 520 may include controls for controlling an actuator positioning the sliding base 504 on the track 502, controlling a phaco-vit vacuum pump, controlling positioning of the gantry 118, controlling positioning of the display 300, controlling information displayed on any of the displays 122, 130, 300, 514, or controlling any other item of equipment included on the operating room equipment 100.

The base 504 may provide a space for routing of tubing and wires between the central base 108 and the sliding base 504 in order to reduce clutter and remove tripping hazards. Tubing and/or wires may then be routed up through the base 504 and arms 510 to components mounted to or resting on the arms 510.

FIG. 6 illustrates electronic components 600 that may be incorporated into the operating room equipment 100. The electronic components 600 may be connected to a data/power bus 602 that enables data communication among the electronic components 600 and supply of electrical power to the electronic components 600.

The electronic components 600 may include a control computing device 604. The control computing device 604 may implement control of actuators incorporated into some or all of the gantry 118, coupled to the arm 302, controlling movement of the sliding base 504, or any other actuators incorporated into the operating room equipment. The control computing device 604 may be programmed to perform coordinated movement of components, such as movement of the gantry 118 and/or display 300 responsive to movement of the sliding base.

The electronic components 600 may include an imaging computing device 606 that receives images captured by the surgical microscope 120, or other imaging device, and displays the images on any of the displays 122, 130, 300, 514. The imaging computing device 606 may process the images in order to generate processed images that are output on any of the displays 130, 300, 514. For example, the processed images may have guides superimposed thereon for guiding performance of ophthalmic surgery, such as placement of incisions, alignment of an IOL, and the like.

The electronic components 600 include one or more imaging devices 608, such as the surgical microscope 120 that provide images to the imaging computing device 606. Other imaging devices 608 may include an optical coherence tomography (OCT) scanner.

The electronic components 600 may include positioning actuators 610. The positioning actuators 610 may include actuators for positioning the gantry 118, the arm 302, the sliding base 504, or other components of the operating room equipment 100.

The electronic components 600 may include one or more displays 612, such as some or all of the display 122, display 130, display 300, and display 514. The electronic components 600 may include a phaco-vit vacuum pump 614. The electronic components 600 may also include the control panel 114.

The electronic components 600 may include electronic components 616 of the surgical chair 126. These electronic components 616 may include the scanner 518, the foot controls 520, and possibly actuators 618 for adjusting the position and orientation of the surgical chair 126, e.g., height, forward/backward positioning, tilt, and position and height of arms 510, position of accessories 512, 514, 516, 518, and position of foot controls 520.

The electronic components 600 may include electronic components of the patient bed 128. The patient bed 128 may include one or more actuators 620, such as actuators for raising and lowering of the platform **128*a* of the patient bed 128 or for changing the angle of portions of the platform. The electronic components of the patient bed 128 may include sensors 622, such as sensors for detecting whether the patient bed 128 is connected to the plug 400, the position of the platform 128*a* of the patient bed 128, or other attributes of the patient bed 128. The electronic components may further include a storage device 624. As noted above, the storage device 624 may be a storage device alone or may be incorporated into a computing device housed within the patient bed 128**.

Various other electronic components 600 may be incorporated. For example, the electronic components 600 may include sensors for monitoring stress of the surgeon and a computing device (which may be the control computing device 604) programmed to receive and process the outputs of these sensors. The electronic components may include sensors for monitoring vitals and stress of a patient and a computing device (which may be the control computing device 604) programmed to receive and process the outputs of these sensors. The outputs from any of these sensors may be used to generate content displayed on any of the displays 122, 130, 300, 514 or output on another output of device, such as emitted by a speaker. The sensors for monitoring vitals and stress of the patient may include a Galvanic skin response wristband, which may include other physiological sensors such as a heart rate sensor.

Figure 7:
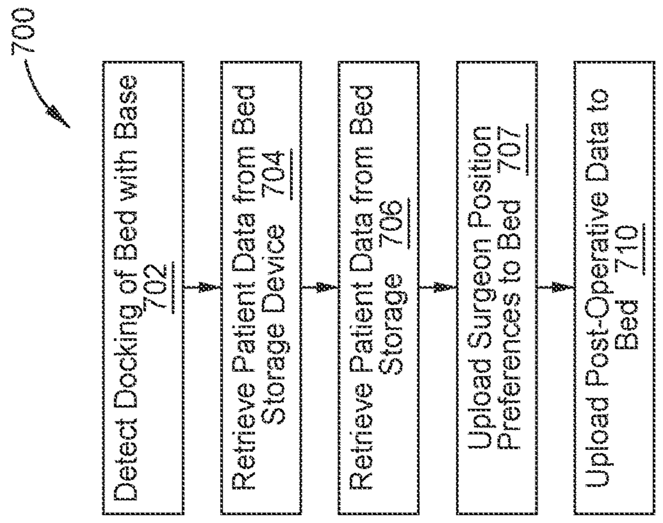
FIG. 7 is a process flow diagram of a method for exchanging data between an electronic patient bed and the operating room equipment in accordance with certain embodiments.

FIG. 7 illustrates a method 700 that may be performed using the operating room equipment 100. The method 700 may be performed by the control computing device 604 or other component of the electronic components 600. The method 700 includes detecting, at step 702, docking of the patient bed 128 with the plug 400. Step 702 may include detecting the storage device 624 connected to the plug 400. The method 700 includes retrieving, at step 704, patient data from the storage device 624 of the patient bed 128. As noted above, the patient data may include a treatment plan for an ophthalmic surgery to be performed using the operating room equipment 100. The patient data may additionally or alternatively include pre-operative diagnostics and analysis. In particular, the surgical microscope 120 in combination with the imaging computing device 606 may display guidance for performing ophthalmic surgery on one or more of the displays 612 or on an internal display of the surgical microscope 120.

The method may further include uploading, at step 708, surgeon preferences for positioning the platform **128*a* of the patient bed 128. Step 708 may include either (a) uploading the preferences to the patient bed 128, such as a computing device incorporated into the patient bed, and the computing device will then implement the preferences by activating the actuators 620 of the patient bed or (b) the control computing device 604 sends control signals to the actuators 620 in order to implement the surgeon preferences. In this manner, a surgeon can ensure that the patient is positioned at a preferred height when performing ophthalmic surgery without needing to manually adjust the height of the platform 128*a* of the patient bed 128. The actuators 620 may control other components of the patient bed 128**, such as headrest position, spinal support positioning, and knee bolster positioning.

In some implementations, the method 700 further includes uploading, at step 710, post-operative data to the storage device 624 of the patient bed 128, thereby ensuring that a copy of the post-operative data is created and is associated with the patient.

The apparatus and methods described above provide the following advantages:

- Reduced floor space usage as components are incorporated into the central base 108 and coupled to a common power bus.
- Improved ergonomics due to the highly-adjustable gantry 118 and improved surgical chair 126.
- Reduced cost as many items of surgical equipment are incorporated into a single stand-alone support structure that does not require modification of the operating room itself and that can be acquired as a single unit.
- Integration of various items of equipment into a single stand-alone structure thereby improving safety due to reduced clutter and tripping hazards from exposed wires and tubing.
- Improved workflow as items of equipment either don't need to be moved or are provided with adjustable mounting points as discussed above, including the various displays and surgical equipment mounted to the gantry 118 that can be easily moved into and out of a surgical area with little effort.

Improved data security due to storage of patient data within the patient bed 128 and transfer of patient data without wireless connections.

Improved image stability and faster image stabilization from the stiffness of the boom 106 and weight of the central base 108, including the weight of electronic components housed in the central base 108.

Reduced noise due to housing of fans within the central base 108 and lateral bases 110*a*, 110*b* and due to the rearward facing exhaust vents.

Improved tubing management by integration of the phaco-vit pump 614 into the central base 108 and the control panel 114 into the boom 106 as well as the ring 512 incorporated into the surgical chair 126.

A modular design in which various items of surgical equipment may be selectively mounted to the gantry 118 or surgical chair 126.

A surgical chair 126 having integrated and adjustable mount points for holding multiple items of surgical equipment at ergonomic positions.

Additional Considerations

The preceding description is provided to enable any person skilled in the art to practice the various embodiments described herein. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates transfer of a computer program from one place to another. The processor may be responsible for managing the bus and general processing, including the execution of software modules stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer readable storage medium with instructions stored thereon separate from the wireless node, all of which may be accessed by the processor through the bus interface. Alternatively, or in addition, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module, it will be understood that such functionality is implemented by the processor when executing instructions from that software module.

The following claims are not intended to be limited to the embodiments shown herein, but are to be accorded the full scope consistent with the language of the claims. Within a claim, reference to an element in the singular is not intended to mean “one and only one” unless specifically so stated, but rather “one or more.” Unless specifically stated otherwise, the term “some” refers to one or more. No claim element is to be construed under the provisions of 35 U.S.C. § 112(f) unless the element is expressly recited using the phrase “means for” or, in the case of a method claim, the element is recited using the phrase “step for.” All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. Operating room equipment comprising:
- a base for resting on a floor;
- a boom extending upwardly from the base and extending outwardly from the base in a forward direction;
- a gantry suspended from the boom and having three or more degrees of freedom;
- a surgical instrument mounted to the gantry;
- one or more electrical components mounted in the base, the electrical components configured to support performing ophthalmic surgery;
- an arcuate track for resting on the floor;
- a sliding base mounted to the arcuate track and slidable along the arcuate track;
- a seat mounted to the sliding base; and
- one or more arms rotatably mounted to the sliding base, the one or more arms having secured thereto
- any of a ring for supporting a phaco-vit handpiece, a display device, an instrument holder, and a scanner.

2. The operating room equipment of claim 1, wherein the one or more electrical components include a vacuum pump.

3. The operating room equipment of claim 2, further comprising a control panel mounted to the boom and facing in the forward direction, the control panel defining a connector for coupling a tube to the vacuum pump and defining controls for controlling operation of the vacuum pump.

4. The operating room equipment of claim 1, wherein the one or more electrical components include a computing device.

5. The operating room equipment of claim 4, wherein the surgical instrument comprises a surgical microscope and the computing device is configured to process images from the surgical microscope.

6. The operating room equipment of claim 1, further comprising a vent on a surface of the base facing a rearward direction opposite the forward direction.

7. The operating room equipment of claim 1, wherein the base comprises a central base, a first lateral base, and a second lateral base, the central base between the first lateral base and the second lateral base, the first lateral base and the second lateral base configured to rest on the floor when the central base is resting on the floor and extending outward from the central base in the forward direction.

8. The operating room equipment of claim 1, wherein the base contains ballast.

9. The operating room equipment of claim 1, wherein the gantry has six degrees of freedom.

10. The operating room equipment of claim 1, further comprising:
- a rotatable member secured to the boom, the gantry being suspended from the rotatable member.

11. The operating room equipment of claim 10, further comprising a shaft that is slidably and rotatably mounted to the rotatable member, the gantry being mounted to the shaft.

12. The operating room equipment of claim 1, further comprising:
- a first electrical coupler connected to the one or more electrical components; and
- a patient bed housing a storage device, the patient bed including a second electrical coupler connected to the storage device and configured to engage the first electrical coupler.

13. The operating room equipment of claim 12, wherein the one or more electrical components include a computing device configured to:
- detect connection of the second electrical coupler to the first electrical coupler; and
- in response to detecting connection of the second electrical coupler to the first electrical coupler, download patient data from the storage device.

14. Operating room equipment comprising:
- a base for resting on a floor;
- a boom extending upwardly from the base and extending outwardly from the base in a forward direction;
- a gantry suspended from the boom and having three or more degrees of freedom;
- a surgical instrument mounted to the gantry;
- one or more electrical components mounted in the base, the electrical components configured to support performing ophthalmic surgery;
- an arcuate track for resting on the floor;

a sliding base mounted to the arcuate track and slidable along the arcuate track;

a seat mounted to the sliding base; and one or more foot controls mounted to the sliding base.

15. The operating room equipment of claim 14, wherein the foot controls are configured to control the surgical instrument.

* * * * *